United States Patent [19]

Lorch

[11] 4,162,687
[45] Jul. 31, 1979

[54] DENTAL FLOSSING DEVICE

[76] Inventor: Leonard G. Lorch, 1352 Emerson St., Palo Alto, Calif. 94301

[21] Appl. No.: 912,951

[22] Filed: Jun. 6, 1978

[51] Int. Cl.² .............................................. A61C 15/00
[52] U.S. Cl. ...................................................... 132/91
[58] Field of Search ..................................... 132/89–93

[56] References Cited
U.S. PATENT DOCUMENTS

| 918,281 | 4/1909 | Chambers | 132/91 |
|---|---|---|---|
| 2,180,522 | 11/1939 | Henne | 132/91 |
| 3,378,017 | 4/1968 | Stiles | 132/92 R |
| 3,897,795 | 8/1975 | Engel | 132/89 |
| 4,013,085 | 3/1977 | Wright | 132/89 |
| 4,034,770 | 7/1977 | Trecker | 132/92 A |

Primary Examiner—G. E. McNeill

[57] ABSTRACT

A flossing device is provided having a handle with a pair of resilient arms. Fingers extend from the arms and the longitudinal axes of the fingers form an angle of between 30° and 180° with each other. Each finger has a knob at its distal end. A length of flossing material is provided which is connected at each end to a grommet so that the flossing material and grommets can be readily attached and detached from the device. A safety strand is also provided which resists cutting of the user's gums by the flossing material.

6 Claims, 7 Drawing Figures

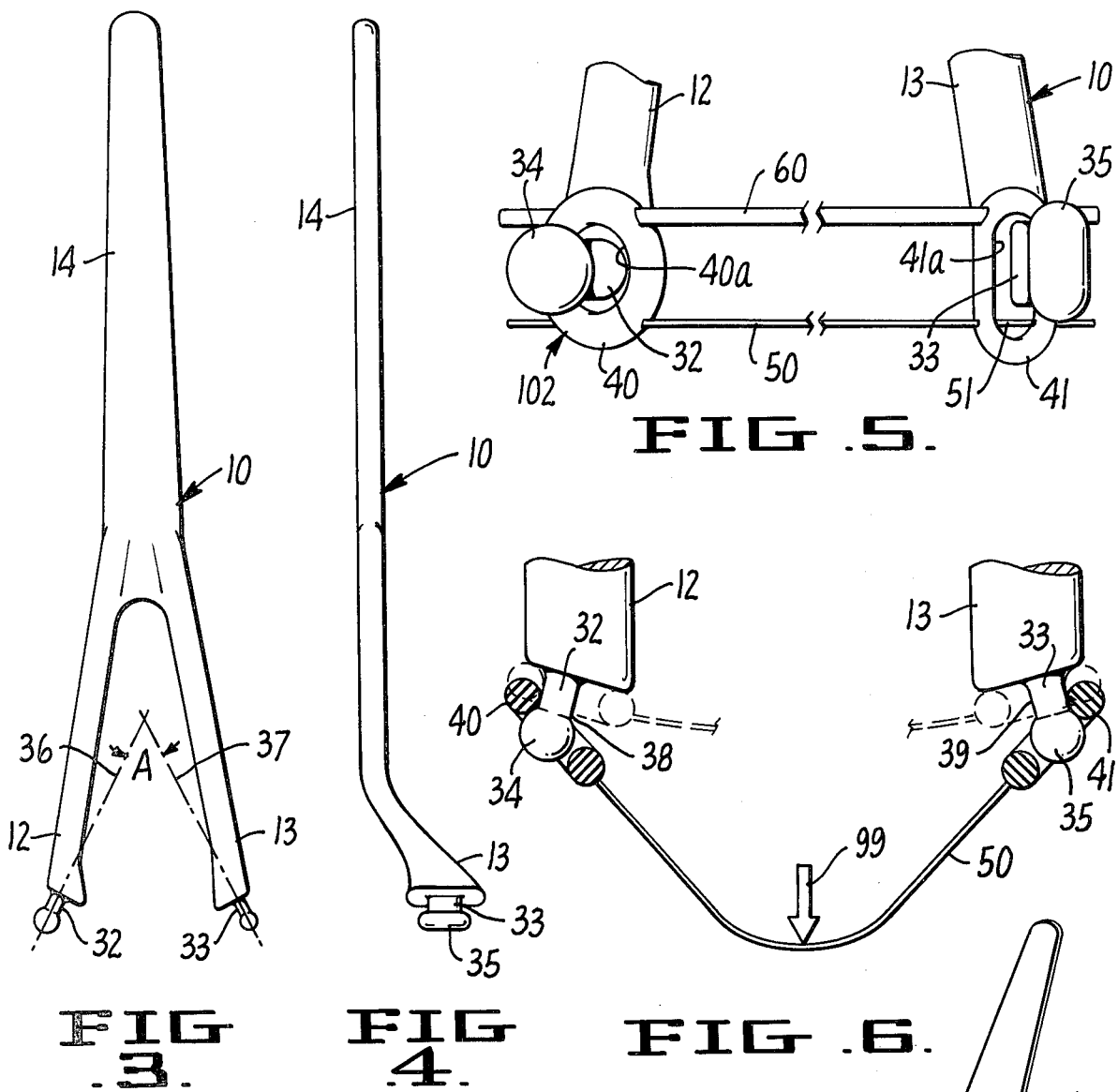

DENTAL FLOSSING DEVICE

This invention relates to flossing devices in general and in particular to a flossing device upon which the flossing material is readily loaded and unloaded, which can be used in one hand, the user does not have to place his fingers inside his mouth while flossing, and which provides safety features for the user.

The prior art includes numerous dental flossing devices, most of which differ from the instant invention in that they are much more difficult to load, do not include the safety features of the present invention, and are more difficult and expensive to manufacture.

The Roth U.S. Pat. No. 788,947 teaches a device for removing obstructions from between the teeth which is much more difficult to load than the instant invention. The Henne U.S. Pat. Nos. 2,180,522 and 2,187,899 teach disposable bows differing from the instant invention in that the disposable portion of the device is more complicated and expensive, and does not have the safety features of the instant invention. Turenchalk U.S. Pat. No. 2,384,712 teaches a floss holder which is much more difficult to load than the instant invention. Buscarino U.S. Pat. No. 2,443,415 discloses a much more complicated system than the instant invention, more expensive to manufacture and more difficult to load. Turenchalk U.S. Pat. No. 2,463,660 teaches a device which is much more difficult to load than the instant invention. De Mar U.S. Pat. Nos. 2,702,555 and 2,702,556 teach methods of securing dental floss in a holder not pertinent to the instant invention. U.S. Pat. No. 3,388,831 relates to a shaving unit and discloses in column 6, lines 15–20 the use of a collet and wedge or resilient button to change a shaving unit, but does not suggest that these devices can be used in dental flossing systems. Nissen U.S. Pat. No. 4,026,016 discloses a pivoting fixed geometry shaving unit, but is not pertinent to dental flossing or to the deformable geometry of the present invention. Morin U.S. Pat. No. 3,420,929 teaches a method of anchoring a monofilament to a plastic injection molding, which relates peripherally to the instant invention in that the locking mechanism shown in FIG. 3 shows a transverse cross head forming a lock by frictionally engaging the rounded portion of an aperture, whereas the instant invention forms a locking mechanism by the flossing or safety strand being so positioned in a grommet to frictionally engage a knob over which the grommet is pressed. Cappello U.S. Pat. No. 3,474,799 discloses a flossing system using twin projections to anchor the section of floss which is more difficult to load than the instant invention. Espinosa U.S. Pat. No. 3,631,869 discloses a flossing device in which the projecting fingers are parallel and more difficult to load than the instant invention which utilizes diverging fingers. Adams U.S. Pat. No. 3,696,821 discloses a rather simple system for application to the fingertips of the user, which requires the user to use both hands during the flossing procedure whereas with the instant invention flossing can be done with one hand. Warren U.S. Pat. No. 3,754,332 discloses a rather simple wedge-shaped device (FIG. 10) for applying chemicals between the teeth which is not pertinent to the instant invention for flossing. Espinosa U.S. Pat. No. 3,769,396 discloses a method for preparing measured lengths of dental floss which is not pertinent to the instant invention. Wesley U.S. Pat. No. 3,802,445 teaches a tooth cleaning appliance having a pair of loops for application to the user's fingers. The instant invention differs from Wesley in that the instant invention can be used easily with one hand and it is not necessary for the user to place his fingers in his mouth during the flossing procedure.

A flossing system developed by the named inventor herein utilizes the linkage of U.S. Pat. No. 3,805,335 (FIG. 3) to be inserted into receptacles in the end of and in line with a pair of diverging arms forming an angle of 20°. The instant invention differs from that prior art system in that the instant invention utilizes a pair of grommets to connect the flossing material and the knobs corresponding to enlargement 16 of U.S. Pat. No. 3,805,335 are permanently affixed to the arms of the instant invention, whereas in the prior art system, the knobs and their supporting shanks as well as interconnecting floss had to be detached from the handle, which was a much more complicated procedure than that of the instant invention. This prior art system does not have diverging fingers forming the necessary angle of between 30° and 180°.

Ely U.S. Pat. No. 3,828,804 teaches a device for cleaning between the teeth which is much more difficult to load than the instant invention in that the strand must be carefully located in slots at the distal end of the projecting fingers. Chien U.S. Pat. No. 3,834,404 teaches a flossing apparatus much utilizes a bobbin and parallel arms which is much more difficult to load than the instant invention. Clark U.S. Pat. No. 3,850,182 teaches a dental floss holder for use on a toothbrush which utilizes parallel arms and which is much more difficult to load than the instant invention. Johnston U.S. Pat. No. 3,901,251 discloses another system for use on the tips of the user's fingers which is more difficult to use than the instant invention. The locking mechanism for the floss around each finger disclosed by Johnston at column 4 is simply wrapping the floss several times around the finger piece. The locking mechanism of the instant invention is provided in a wholly different manner. Jenkins U.S. Pat. No. 3,906,963 discloses a very complicated system for applying dental floss from a spool to the tips of the holder. The instant invention is much simpler and cheaper to manufacture than Jenkins. Katz U.S. Pat. No. 3,926,201 discloses a dental floss applicator in which the entire device is disposable. The Katz device is not nearly as versatile as the instant invention and does not contain the safety features of the present invention. Spanondis U.S. Pat. No. 3,939,853 discloses a flossing device which utilizes a pair of parallel arms and feeds dental floss to the distal end of the device. The present invention is much simpler in construction and much easier to load with a new section of flossing material. Spanondis teaches a rather crude safety portion 26 in column 6 of his specification. The safety strand of the instant invention differs substantially from the bulbed fulcrum 26 of Spanondis. Chodorow U.S. Pat. No. 3,974,842 discloses a flossing tool which is disposable and which does not have the versatility or the safety features of the present invention. Chodorow U.S. Pat. No. 4,006,750 differs from the instant invention in the same respects as his earlier patent. Wright U.S. Pat. No. 4,013,085 teaches a device which is more difficult to load than the present invention and which is not as versatile as the present invention. Chodorow U.S. Pat. No. 4,016,892 teaches a length of floss with tabs at either end, which is not pertinent to the present invention. Trecker U.S. Pat. No. 4,034,770 teaches conventional dental floss with loops therein, not pertinent to the present invention.

Andren U.S. Pat. No. 1,091,789 teaches a multiple strand instrument which is not pertinent to the present invention. Waters U.S. Pat. No. 3,421,524 teaches a dental cleaner which is much more complicated than the present invention.

It is also known in the prior art to impregnate flossing material with flavoring, aromatic or medicament and to coat with a flavoring. It is also known in the prior art that a length of flossing material may be a hybrid floss invented by periodontist Pesce, U.S. Pat. No. 3,789,858, having a conventional floss material to allow or prevent the stretch of a tufted floss material where said stretchable floss material is comprised of a non-tufted section of smaller diameter in order to pass through the contact point and a section of large tufted diameter where the greater surface area and rougher texture significantly brush and remove bacterial plaque. Relatively conventional floss only disturbs bacterial plaque. In this invention, the delivery of the flavoring, aromatic, or medicament is accomplished by a safety strand, not by the flossing material.

The instant invention provides a flossing device which is extremely simple, can be used by one hand, can be readily loaded and unloaded with one hand and provides a variety of safety features.

A primary object of the instant invention is to provide a flossing device upon which the flossing material can be readily loaded and unloaded with one hand.

A further object of the invention is to provide a flossing device simple in construction but which utilizes disposable sections of flossing material.

A further object of the invention is to provide a flossing device in which the user does not have to place his fingers in his mouth during the flossing procedure.

A further object of the invention is to provide a flossing device which utilizes a safety strand to resist cutting of the user's gums during the flossing procedure.

A further object of the invention is to provide a flossing device in which the surfaces used inside the mouth are smooth and present relatively little safety hazard to the user.

A further object of the invention is to provide a flossing device upon which disposable units of flossing material may be readily applied and a storage tray which efficiently and inexpensively stores flossing material.

Further objects and advantages of the invention will become apparent from the following description and from the drawings wherein:

FIG. 3 is a plan view of the instant invention;

FIG. 4 is a side elevational view of the invention;

FIG. 5 is a perspective view of a portion of the invention;

FIG. 6 is a schematic representation of a portion of the invention; and

FIG. 7 is a perspective view of the storage tray used with the invention.

Figure 1:
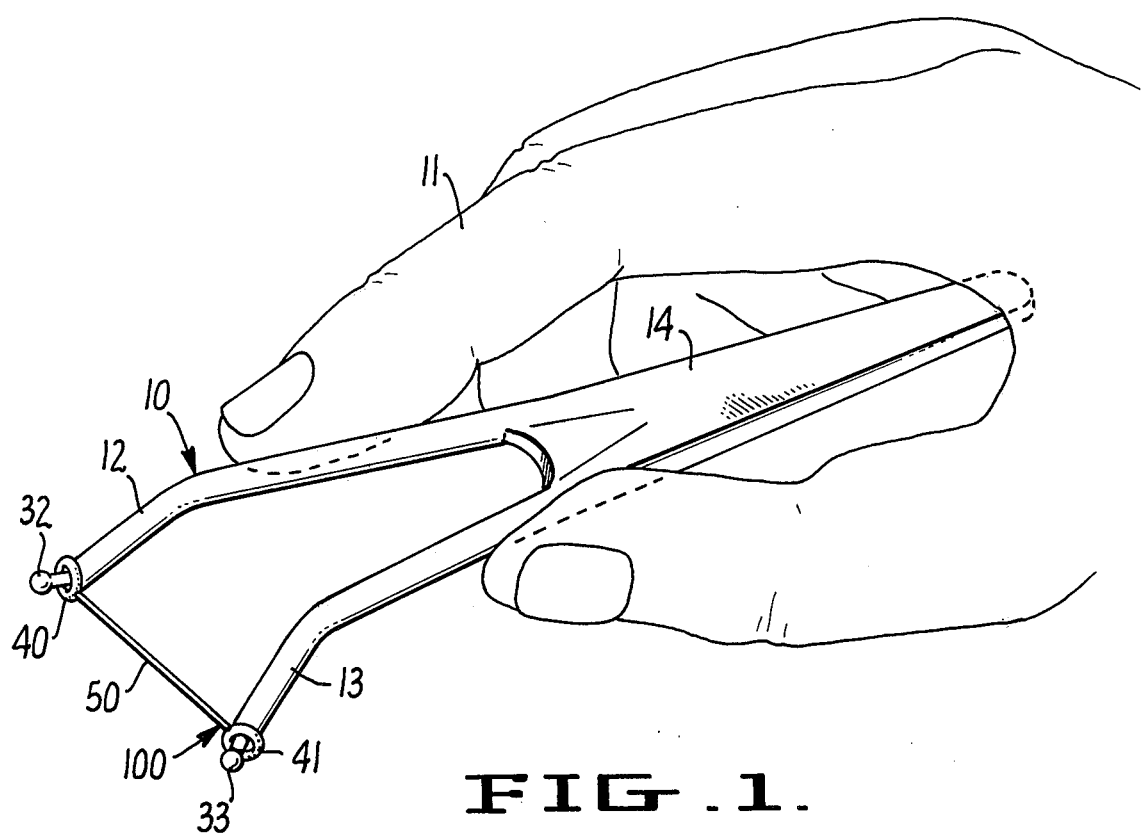
FIG. 1 is a perspective view of the invention.
Figure 2:
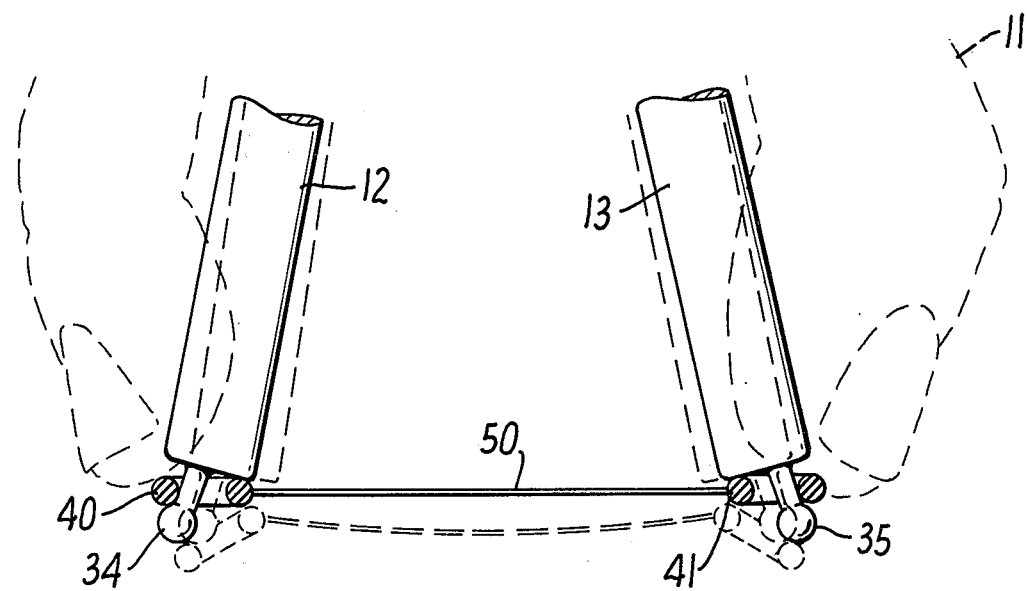
FIG. 2 is a schematic representation of the loading and unloading feature of the instant invention.

Referring to the drawings, FIG. 1 shows the device 10 as held in the user's hand 11. For the desired resilience, device 10 is molded with a glass filled polycarbonate, e.g., General Electric's LEXAN brand or Part No. LNP DF 1002 belonging to the Liquid Nitrogen Processing Company, Santa Ana, California. A pair of resilient arms 12 and 13 extend from a handle 14. Each of the arms 12 and 13 has a finger 32 and 33 extending therefrom respectively. A pair of grommets 40 and 41 are connected to the ends of a length of flossing material 50. Grommets 40 and 41 and the length of flossing material 50 connected therebetween is a disposable unit 100. FIG. 2 shows generally how grommets 40 and 41 and the length of flossing material 50 is loaded and unloaded from arms 12 and 13. As the user presses resilient arms 12 and 13 toward each other, the centers of grommets 40 and 41 become aligned with knobs 34 and 35, respectively, carried on the ends of arms 12 and 13. The centers of grommets 40 and 41 are spaced apart a distance less than the distance between centers of grommet retaining means or knobs 34 and 35 to facilitate loading and unloading by urging resilient arms 12 and 13 toward each other.

FIG. 3 is a plan view of the device 10 which shows longitudinal axes 36 and 37 of fingers 32 and 33, respectively. Axes 36 and 37 form an angle A of between 30° and 180° with each other with the preferred angles being between 45° and 120°.

FIG. 4 is a side elevational view of the device 10 showing an oblong knob 35 carried on the end of finger 33.

FIG. 5 shows the device 10 incorporating a safety strand 60 connected to grommets 40 and 41 in addition to the length of flossing material 50 forming a disposable unit 102. Safety strand 60 is spaced apart from flossing material 50 so that the safety strand 60 in use will ride on the occlusal surfaces of the user's teeth and resists cutting of the user's gums by flossing material 50. A preferred embodiment of safety strand 60 is a braided Nylon cord, e.g., Part No. 840-8R from the Woodstock Line Company, Putnam, Conn. Safety strand 60 can be a monofilament molded at the time grommets 40 and 41 are molded.

Spherical knob 34 is carried at the distal end of finger 32 and engages circular grommet 40 which has an inner diameter 40a which exceeds the outer diameter of knob 34. FIG. 5 shows an oval knob 35 carried at the distal end of finger 33 and an oval grommet 41 with an inner periphery 41a which exceeds the periphery of knob 35. The grommets can be of alternate design, for example, hinged ties, press fit grommets or split grommets. Knob 35 may be spherical in design as is knob 34 and grommet 41 in that instance would preferably be circular in design as is grommet 40.

FIG. 6 shows how grommets 40 and 41 pivot or articulate with respect to fingers 32 and 33. Fingers 32 and 33 have shanks 38 and 39, respectively, of sufficient length to allow grommets 40 and 41 to pivot or rotate from the position shown in phantom in FIG. 6 to the alternate positions shown in FIG. 6. It is understood that in the alternate position shown in phantom, arms 12 and 13 are spread further apart. Arrow 99 represents a deflecting force caused by a contact point, for example. Such articulating is necessary during the course of using the device 10 with the human dentition as it is desirable to move the device longitudinally, laterally, axially and other directions. By providing shanks 38 and 39 of sufficient length, grommets 40 and 41 pivot as shown in FIG. 6 without becoming dislodged from fingers 32 and 33.

To assist in retaining grommets 40 and 41, as shown in FIG. 5, a section 51 of flossing material 50 extends through the inner diameter or inner periphery 41a of grommet 41, thereby forming a locking mechanism retaining grommet 41 on knob 35. Section 51 of flossing material 50 is positioned so that it frictionally engages knob 35 and slight pressure must be exerted to place grommet 41 on knob 35 and to remove it from knob 35. This locking mechanism may be used on both grommets simultaneously (when no safety strand is used) or on one grommet as shown. The locking mechanism prevents grommet 41 from falling off knob 35 should the flossing material 50 fray or break in use, particularly when safety strand 60 is not utilized. When safety strand 60 is utilized, if flossing material 50 breaks or frays while in use, disposable unit 102 will remain on knobs 34 and 35 without the assistance of the locking mechanism provided by section 51 of flossing material 50. Furthermore, use of the locking mechanism facilitates the use of a length of flossing material wherein the centers of the grommets are spaced apart a distance which exceeds the distance between centers of the grommet retaining means. When the locking mechanism is used, simply urging arms 12 and 13 toward each other (FIG. 2) does not detach the grommets from the grommet retaining means. To detach the grommets, it is necessary to force the grommets off the grommet retaining means, for example, by pushing or pulling with the user's fingers.

Safety strand 60 may be impregnated with or coated with such substances as flavor oils, aromatics or medicaments such as a fluoride compound to be delivered to the occlusal surfaces of the dentition. Safety strand 60 and/or flossing material 50 may be coated with edible substances such as ice cream, frozen peanut butter, frozen fruit juices, candy, carob, cheese, iced tea and coffee. The coating may be uneven, i.e., the substances may be formed in bulbs.

FIG. 7 shows a storage tray 70 containing a plurality of pairs of grommets such as 40 and 41 connected by individual and disposable lengths of flossing material 50. Tray 70 may be designed to store only one pair of grommets and one length of flossing material. A relief cushion 80 is provided under storage tray 70 to facilitate loading of a given length of flossing material onto flossing device 10. One hand of the user simply positions fingers 32 and 33 over grommets 40 and 41, urges resilient arms 12 and 13 toward each other and presses fingers 32 and 33 downwardly against relief cushion 80 to load the length of flossing material onto the device 10. The relief cushion 80 can be the closed cell "ETHAFOAM" cushion manufactured by Dow Chemical, Midland, Michigan. Alternately, the free hand, not shown, opposite hand 11 may be used to provide a relief cushion substitute where the flesh of the free hand is used. The device is then ready for use and upon completion of use, the length of flossing material is discarded.

Where angle A is between approximately 100° and 180°, disposable units 100 and 102 can be loaded without using a relief cushion 80, because grommets 40 and 41 contact and pivot onto shanks 38 and 39, and in this case, knobs 34 and 35 are not necessary.

The safety strand 60 can be used reversably and safely as a secondary and large cross section flossing material between teeth spaced wider apart lacking a contact point. That is, the handle 14 can be reversed or the disposable unit 102 may be reversed.

Virtually all surfaces of the device which are utilized inside the user's mouth are rounded and smooth to minimize hazards to gum tissue and mucosal tissue in using the device.

I claim:

1. A device for flossing teeth comprising:
a handle with a pair of resilient arms extending therefrom, each of said arms having a finger extending therefrom, the longitudinal axes of said fingers forming an angle of between 30° and 180° with each other;
grommet retaining means carried by each arm;
a length of flossing material; and
a pair of grommets connected to the ends of said flossing material, such that said grommets are readily attached to and detached from said grommet retaining means by sliding onto and off said grommet retaining means and being held in position on said grommet retaining means by the diverging angle formed by said fingers.

2. The device of claim 1 wherein the centers of said grommets are spaced apart a distance less than the distance between centers of said grommet retaining means.

3. The device of claim 1 further comprising a safety strand which is connected to said pair of grommets and which is spaced apart from said flossing material so that the safety strand rides over the occlusal surfaces of the teeth and resists cutting of the user's gums by said flossing material.

4. The device of claim 1 wherein said grommet retaining means comprises:
a knob mounted on each of said fingers, and wherein:
each of said fingers has a shank of sufficient length to allow said grommets to articulate thereon without becoming dislodged.

5. The device of claim 4 wherein said flossing material extends through the inner diameter of one of said grommets, forming a locking mechanism retaining said grommet on said knob.

6. The device of claim 3 wherein said safety strand extends through the inner diameter of one of said grommets, forming a locking mechanism retaining said grommet on said finger.

* * * * *